US008772346B2

(12) United States Patent
Gour et al.

(10) Patent No.: US 8,772,346 B2
(45) Date of Patent: Jul. 8, 2014

(54) PHARMACEUTICAL COMPOSITION

(75) Inventors: Samanta Gour, Gujarat (IN); Nanda Nagesh, Gujarat (IN)

(73) Assignee: Torrent Pharmaceuticals Limited, Gujarat (IN)

( * ) Notice: Subject to any disclaimer, the term of this patent is extended or adjusted under 35 U.S.C. 154(b) by 591 days.

(21) Appl. No.: 12/097,453

(22) PCT Filed: Nov. 9, 2006

(86) PCT No.: PCT/IN2006/000447
§ 371 (c)(1),
(2), (4) Date: Oct. 15, 2008

(87) PCT Pub. No.: WO2007/069274
PCT Pub. Date: Jun. 21, 2007

(65) Prior Publication Data
US 2009/0298944 A1     Dec. 3, 2009

(30) Foreign Application Priority Data
Nov. 9, 2005    (IN) .................. 1404/MUM/2005

(51) Int. Cl.
*A61K 31/13*    (2006.01)
*A61K 31/135*    (2006.01)

(52) U.S. Cl.
USPC ........................... 514/645; 514/646; 514/649

(58) Field of Classification Search
USPC ........................ 514/645, 646, 649
See application file for complete search history.

(56) References Cited

U.S. PATENT DOCUMENTS

| 5,510,118 | A | * | 4/1996 | Bosch et al. | 424/489 |
| 5,773,029 | A | * | 6/1998 | Chiesi et al. | 424/488 |
| 6,500,867 | B1 | * | 12/2002 | Virkki et al. | 514/646 |
| 6,511,678 | B2 | * | 1/2003 | Qiu et al. | 424/464 |
| 2003/0077297 | A1 | * | 4/2003 | Chen et al. | 424/400 |

FOREIGN PATENT DOCUMENTS

| WO | 0015196 | 3/2000 |
| WO | 0059475 | 10/2000 |
| WO | 2004026309 | 4/2004 |
| WO | 2004032906 | 4/2004 |
| WO | 2004089353 | 10/2004 |

OTHER PUBLICATIONS

Savolainen, J, Effects of Aqueous Solubility and Dissolution Characteristics on Oral Bioavailability of Entacapone, Drug Development Research 49:238-244 (2000).

* cited by examiner

*Primary Examiner* — Raymond Henley, III
(74) *Attorney, Agent, or Firm* — Dennis A. Bennett; Brock Levin

(57) ABSTRACT

The present invention relates to a pharmaceutical composition of practically water insoluble or low water soluble compounds containing catechol moiety by enhancing the solubility of such compounds using one or more alkalizing agent and optionally adding one or more pharmaceutically acceptable excipient. The present invention also relates to a process for preparing such pharmaceutical composition.

3 Claims, No Drawings

PHARMACEUTICAL COMPOSITION

FIELD OF THE INVENTION

The present invention relates to a pharmaceutical composition of practically water insoluble or low water soluble compounds containing catechol moiety by enhancing the solubility of such compounds using one or more alkalising agent.

The present invention also relates to a process for preparing such pharmaceutical composition

BACKGROUND OF THE INVENTION

Low-solubility drugs often show poor bioavailability or irregular absorption, the degree of irregularity being affected by factors such as dose level, fed state of the patient, and form of the drug. Increasing the bioavailability of low-solubility drugs has been the subject of much research. Increasing bioavailability hinges on improving the concentration of the drug in solution to improve absorption.

It is known that many low-solubility drugs can be formulated so as to increase the maximum concentration of the drug that will dissolve in an aqueous solution in in-vitro tests. It has been shown that when such forms are tested in vivo they can enhance the relative bioavailability of the drug, presumably by enhancing, at least temporarily, the concentration of dissolved drug present in the gastrointestinal (GI) tract.

Another approach is that some low-solubility drugs may be formulated in highly soluble salt forms that provide temporary improvements in the concentration of the drug in a use environment relative to another salt form of the drug. An example of such a drug is sertraline, which in the lactate salt form has a higher aqueous solubility at pH 3 than the HCl salt form. Use of water soluble acid addition salt of poorly soluble drug is disclosed in U.S. Pat. No. 5,441,747.

It is known that other drug form known to provide, increased concentrations in solution of low-solubility drugs consists of drug in a hydrate or solvate crystalline form of the drug. Such forms often have higher aqueous solubility relative to the lowest solubility crystalline form and, therefore, provide higher concentrations of drug. Polymorphs comprise another drug form that temporarily provides increased concentrations in solution. Some polymorphs, also referred to herein as "high-energy crystalline forms," have higher aqueous solubility and therefore can provide enhanced aqueous concentration of the drug relative to other crystal structures and relative to the equilibrium concentration.

It is also well known that the amorphous form of a low-solubility drug that is capable of existing in either the crystalline or amorphous form may also temporarily provide a greater aqueous concentration of drug relative to the equilibrium concentration of drug in a use environment. It is believed that the amorphous form of the drug dissolves more rapidly than the crystalline form, often dissolving faster than the drug can precipitate from solution. As a result, the amorphous form may temporarily provide a greater-than equilibrium concentration of drug.

Another method that can temporarily provide a greater than equilibrium drug concentration is to include a solubilizing agent such as citric acid, etc. in the drug form. Such solubilizing agents promote the aqueous solubility of the drug. An example of the use of a solubilizing agent with a drug to increase aqueous solubility is the use of solubilizing agents with sertraline. As disclosed in PCT Application No. 99/01120, when sertraline is co dissolved in aqueous solution with a solubilizing agent, for example, citric acid, the solubility of sertraline is dramatically increased.

Yet another technique for temporarily achieving a greater than equilibrium concentration of drug in a use environment is to formulate the drug as an aqueous or organic solution. For example, drug can be dissolved in polyethylene glycol (PEG) or an aqueous solution of PEG to which an acid or base may be added or the drug may be dissolved in an aqueous solution of an acid or base. Alternatively, the drug can be dissolved in a pharmaceutically acceptable organic liquid such as glycerol, mono-, di-, or triglycerides, fats or oils.

Another approach to increase the bioavailability of low-solubility drugs has involved forming amorphous dispersions of drugs with polymers. Examples of attempts to increase drug concentration by forming a dispersion of the drug with a polymer include Lahr et al., U.S. Pat. No. 5,368,864, Kanikanti et al., U.S. Pat. No. 5,707,655 and Nakamichi et al., U.S. Pat. No. 5,456,923. However, creating an amorphous dispersion of a drug and polymer(s) does have some drawbacks. For example, some drugs may degrade at the elevated temperatures used to form some dispersions. Some processes use organic solvents, which must be thoroughly removed to avoid drug degradation.

Increasing drug solubilization by using combinations of drug and polymer has also been described. For example, Martin et al., U.S. Pat. No. 4,344,934 mixed poorly-soluble drugs with polymers such as hydroxypropyl methyl cellulose (HPMC) and added an aqueous surfactant solution to the drug-polymer mixture. While this results in improved dissolution, there is only slight enhancement of drug concentration relative to the equilibrium concentration. Particle size reduction of active principle may also improve the bioavailabilty.

It is desirable that active pharmaceutical ingredient is released from the oral composition as soon as possible after ingesting it. This can normally be achieved by using a solublisation enhancing agent in the pharmaceutical composition. The solublisation enhancing agent may be a disintegrant, surface active agent or any other agents that enhance the solublisation. There is vast selection of different solublisation enhancing agents, including disintegrants, on the market, which have different chemical and physical characteristics. When selecting the best solublisation enhancing agent to be used in the pharmaceutical composition in combination with active agent, numerous factors have to be considered, e.g. the chemical and physical characteristics of the active agents, and solublisation enhancing agent, the chemical and physical characteristics of the auxiliary agents, such as diluents and binder, the method of preparing the composition, etc.

Various compound containing catechol moiety like entacapone, nitecapone, tolcapone or a pharmaceutically acceptable salt thereof, are used as active pharmaceutical ingredient are practically insoluble in water. Because of this property, dissolution of the product & bioavailability is always a challenge to develop the product in formulation.

Entacapone is an inhibitor of catechol-O-methyltransferase (COMT), used in the treatment of Parkinson's Disease as an adjunct to levodopa/carbidopa therapy.

Formulations of solid medicinal forms with the active ingredient entacapone, nitecapone or pharmaceutically acceptable salts thereof have already been described in U.S. Pat. No. 6,599,530. It was found that croscarmellose sodium can be used in an amount of at least 6% by weight of the composition to resolve the poor dissolution of entacapone, nitecapone or pharmaceutically acceptable salts thereof. Croscarmellose sodium is required for satisfactory dissolution as compared to other common dissolution-improving agents such as sodium lauryl sulphate, sodium starch glycolate, starch, pregelatinized starch, microcrystalline cellulose or mannitol. According to this invention, the poor dissolution problem of entacapone can be resolved by using croscarmellose sodium in an amount of at least 6% by weight of the composition. This patent justifies use of croscarmellose sodium in the marketed product.

Entacapone Tablet is available in US and elsewhere under the trade name of COMTAN®

The inactive ingredients of the COMTAN® Tablet are microcrystalline cellulose, mannitol, croscarmellose sodium, hydrogenated vegetable oil, hydroxypropyl methylcellulose, polysorbate 80, glycerol 85%, sucrose, magnesium stearate, yellow iron oxide, red oxide, and titanium dioxide. Physician's Desk Reference, 59th ed., pp. 2291-2295 (2005)

PRIOR ART

Among the various compounds, entacapone and nitecapone having catechol moiety are described in U.S. Pat. No. 5,446,194 as catechol-O-methyltransferase (COMT) inhibitors. Enteral and parenteral routes of administration are discussed in U.S. Pat. No. 5,446,194.

Crosslinked cellulose derivative like croscarmellose sodium enhances the dissolution of Entacapone in oral compacted dosage form is described in WO 00/15196. The invention relates to an oral compacted composition comprising entacapone, nitecapone, or a pharmaceutically acceptable salt thereof, and croscarmellose sodium (Ac-Di-Sol) as a dissolution-enhancing agent. It was found that crosslinked cellulose derivative like croscarmellose sodium can be used in an amount of at least 6% by weight of the composition to resolve the poor dissolution of entacapone, nitecapone or pharmaceutically acceptable salts thereof. According to this invention croscarmellose sodium is required for satisfactory dissolution as compared to other common dissolution improving agents such as sodium lauryl sulphate, sodium starch glycolate, starch, pregelatinized starch, microcrystalline cellulose or mannitol. According to this invention, the poor dissolution problem of entacapone can be resolved by using croscarmellose sodium in an amount of at least 6% by weight of the composition.

US20060222703 discloses pharmaceutical compositions of entacapone, levodopa & carbidopa along with pharmaceutical excipients, wherein the excipients are long chain polymers having an equilibrium moisture content of at least 2% and the preparation methods.

In a research article, titled as "Effect of aqueous solubility and dissolution characteristics on oral bioavailability of entacapone" (Jouko Savolainen et al. Drug Development Research 2000; 49 {Issue 4}; pages 238-244) discusses about effect of hydroxypropyl-β-cyclodextrin (HP-β-CD) on entacapone. This study shows complexation of entacapone with HP-β-CD (10% w/v) increases the aqueous solubility of entacapone 12 fold and 85 fold at pH 3.0 and at pH 5.0, respectively.

The present inventors have surprisingly found that pharmaceutical compositions of the poorly soluble compounds containing catechol moiety such as Entacapone, nitecapone, tolcapone when formulated along with alkalising agent, and manufactured by a process such as wet granulation exhibited excellent dissolution characteristics and were found to be comparable with respect to the marketed formulation.

It was further surprisingly found that Entacapone could be formulated without using crosslinked cellulose derivative, or binder or disintegrant without affecting the dissolution characteristics of the drug.

OBJECTS OF THE INVENTION

It is an object of the present invention to provide a pharmaceutical composition of practically water insoluble or low water soluble compounds containing catechol moiety by enhancing the solubility of such compounds by using one or more alkalising agent.

Another object of the present invention is to provide a simple granulation process, like wet granulation for manufacturing of solid oral dosage form for practically water insoluble or low water soluble compounds containing catechol moiety.

Yet another object of the present invention is to provide pharmaceutical compositions comprising Catechol derivative as an active ingredient, alkalising agent(s) and one or more adjuvants, to achieve desired dissolution profile.

Yet another object of the present invention is to provide pharmaceutical compositions comprising Catechol derivative as an active ingredient, alkalising agent(s) and one or more adjuvants, without incorporating crosslinked cellulose derivative, to achieve desired dissolution profile.

Yet another object of the present invention is to provide pharmaceutical compositions comprising Catechol derivative as an active ingredient, alkalising agent(s) and one or more adjuvants, without incorporating binder, to achieve desired dissolution profile.

Yet another object of the present invention is to provide pharmaceutical compositions comprising Catechol derivative as an active ingredient, alkalising agent(s) and one or more adjuvants, without incorporating disintegrant, to achieve desired dissolution profile.

Yet another object of the present invention is to provide pharmaceutical compositions comprising Catechol derivative as an active ingredient, alkalising agent(s) and one or more adjuvants, without incorporating crosslinked cellulose derivative, disintegrant and binder, to achieve desired dissolution profile.

Yet another object of the present invention is to provide pharmaceutical compositions comprising active ingredient such as catechol derivatives like entacapone, nitecapone and tolcapone in combination with levodopa, carbidopa or other such compounds, either separately or in a fixed dose combination thereof.

Further object of the present invention to provide process of preparing pharmaceutical composition of practically water insoluble or low water soluble compounds containing catechol moiety.

SUMMARY OF THE INVENTION

Thus according to the first aspect of the present invention there is provided a pharmaceutical composition and its manufacturing process by solubility enhancement of practically water insoluble or low water soluble compounds containing catechol moiety by using one or more alkalising agent.

According to second aspect of the invention the pharmaceutical dosage form is in the form of a tablet, capsule, powder or pellets or parenteral comprising catechol moiety and alkalising agent.

Further, the present invention also provides a solid dosage form of compounds containing catechol moiety, alkalising agent(s), and one or more adjuvants, optionally without using binder and/or disintegrant and a process for preparation of the same.

Additional objects and advantages of the invention will be set forth in part in the description which follows, and in part will be obvious from the description, or may be learned by practice of invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

Applicants have found that alkalising agent is effective for increasing the dissolution rate of practically water insoluble or low water soluble compounds containing catechol moiety. Present invention relates to a pharmaceutical composition of such compounds by enhancing the solubility using one or more alkalising agent.

The present invention also teaches a process for preparing said composition.

An oral dosage form wherein a mixture of an active compound containing catechol moiety was granulated with alkalising agent(s), then mixed with one or more auxiliary agent, and further the blends are tableted or enclosed in capsule. The best dissolution enhancing agent is the one that releases the active ingredient from the dosage form as fast as possible.

Direct compression may be done by blending active ingredient with alkalising agent then mixing with one or more auxiliary agents, and further the blends may be tableted or lubricated blend can be filled in capsule.

Applicants found that alkalising agent is more efficient in releasing active ingredient from the oral dosage form than other common dissolution improving agents, such as sodium lauryl sulphate, polysorbate, starch, mannitol, lactose, pregelatinised starch, microcrystalline cellulose.

The term "drug" or "active ingredient" refers to an agent, active ingredient compound or other substance, or compositions and mixture thereof that provide some pharmacological, often beneficial, effect. Reference to a specific active ingredient shall include where appropriate the active ingredient and it's pharmaceutically acceptable salts.

The term "dosage form" denotes any form of the formulation that contains an amount sufficient to achieve a therapeutic effect.

The term "Practically water insoluble" refers having a solubility of about more than 10,000 parts of solvent required to solubilize one part of drug.

The term "Low water soluble" refers having a solubility of about 30 to 10000 parts of solvent required to solubilize one part of solute.

Compounds having catechol moiety refers to the active ingredient. Examples of compounds having catechol moiety comprises of but not limited to entacapone, nitecapone tolcapone, tretoquinol apomorphine, melevodopa, dobutamine, dopexamine, droxidopa, fenoldopam, keracyanin, methyldopa, papaveroline and their pharmaceutically acceptable salts, esters, polymorphs, hydrates, solvates, enantiomers or mixtures thereof.

Pharmaceutical Composition

A pharmaceutical dosage form of a tablet or capsule or parenteral which comprises a pharmaceutically effective amount of active ingredient containing catechol moiety and alkalising agent.

The present invention also provides a process for preparation of solid dosage form preferably tablet or capsule of catechol derivative with alkalising agent and one or more adjuvants.

Pharmaceutical composition according to the present invention is preferably in the form of a tablet or capsule or parenteral. The active ingredient used in the present pharmaceutical composition is catechol derivative, which is subjected to alkaline environment, dried and optionally sieved.

The solid dosage form tablet or capsule of the present invention is prepared using active ingredient and alkalising agent i.e., catechol derivative with alkalising agent and pharmaceutically acceptable excipients selected from the group comprising of diluents, lubricants, glidants and other pharmaceutically acceptable excipients or adjuvants but without a disintegrant more particularly without a crosslinked cellulose derivative.

The alkalising agent(s), which are to be used in accordance with the invention, are now described. It is only required of such alkalising agents to show basicity (pH of not less than 7) when they are in the form of a 1% aqueous solution or suspension Alkalising agent may be selected from the group comprising sodium dihydrogen phosphate disodium dihydrogen phosphate, trisodium phosphate, sodium bicarbonate, sodium carbonate, sodium hydroxide, potassium hydroxide, potassium hydrogen phosphate, dipotassium hydrogen phosphate, tripotassium phosphate and other materials known for such property. "providing alkaline enviroment" is a process in which the catechol derivative is mixed with alkalising agent(s). The mixing can be dry or wet with suitable vehicle, if required. Alkalising agent in the dosage form ranges from 0.4% to 52.0% by weight.

Diluents may be selected from the group comprising of mannitol, microcrystalline Cellulose, lactose, starch, dibasic calcium phosphate anhydrous, tribasic calcium phosphate, kaolin, sucrose, precipitated calcium carbonate, sorbitol, maltodextrin, powdered cellulose, micro crystalline cellulose and other materials known for such property. Diluents in the dosage form ranges from 0% to 78.0% by weight.

Lubricants may be selected from the group comprising of stearic acid, sodium stearyl fumarate, polyethylene glycol, magnesium stearate, calcium stearate, talc, zinc stearate, hydrogenated castor oil, silica, colloidal silica, cornstarch, calcium silicate, magnesium silicate, silicon hydrogel and other materials known for such property. Lubricants in the dosage form ranges from 0% to 3.0% by weight.

Binders may be selected from the group comprising of polyvinylpyrrolidone, hydroxypropyl methylcellulose, acacia, alginic acid, hydroxy propyl cellulose, carboxymethylcellulose sodium, compressible sugar, ethylcellulose, gelatin, liquid glucose, methylcellulose, pregelatinized starch and other materials known to one of ordinary skill in the art. Binders in the dosage form ranges from 0% to 5.0% by weight.

Glidants may be selected from the group comprising of colloidal silicon dioxide, colloidal silica, cornstarch, talc, calcium silicate, magnesium silicate, colloidal silicon, silicon hydrogel and other materials known for such property. Glidants in the dosage form ranges from 0% to 2.0% by weight.

The pharmaceutical composition may optionally be coated with functional and/or non-functional layers comprising film-forming polymers, if desired. Examples of film-forming polymers include ethylcellulose, hydroxypropyl methylcellulose, hydroxypropylcellulose, polyvinyl alcohol, polyvinyl acetate methylcellulose, carboxymethyl cellulose, hydroxymethylcellulose, hydroxyethylcellulose, cellulose acetate, hydroxypropyl methylcellulose phthalate, cellulose acetate phthalate, cellulose acetate trimellitate; waxes; methacrylic acid polymers and the like. Alternatively, commercially available coating compositions comprising film-forming polymers marketed under various trade names, such as Opadry may also be used for coating. Film-forming polymer in the dosage form ranges from 1.5% to 4.0% by weight.

Other pharmaceutical solvents are selected from the group comprising of methanol, acetone, methylene chloride and purified water.

One skilled in the art would recognize other suitable auxiliary agents, lubricants and glidants that can be used in the composition of present invention.

Catechol derivatives like entacapone, nitecapone and tolcapone may be administered with levodopa or carbidopa or benserazide, either separately or in a fixed dose combination thereof.

The invention will be further clarified by the following examples, which are intended to be purely exemplary of the invention and are not intended to limit the scope of the invention.

General Manufacturing Process

Process A:
1. Sift the drug optionally with suitable excipients through suitable sieve and granulate with alkalizer solution or mix the drug with alkalizer and optionally with suitable excipients and granulate with suitable solvents.
2. Dry the wet granules at suitable temperature and size through suitable sieve.
3. Blend the dried granules with lubricant and optionally with diluents. Fill this blend into capsule or compress the lubricated blend into tablets.
4. Optionally coat the core tablet with coating suspension.

Or

Process B:
1. Sift & Mix the drug with alkalising agent and with at least one pharmaceutically acceptable excipient.
2. Lubricate the blend of step 1 with lubricant.
3. Optionally compress the lubricated blend obtained from step 2 or fill into the capsules.

Or

Process C:
1. Sift & Mix the drug with alkalising agent and with at least one pharmaceutically acceptable excipient.
2. Slug the blend of step 1.
3. Mill and sift the slugs of step 2.
4. Lubricate the blend of step 3 with lubricant.
5. Optionally compress the lubricated blend.

Example-1

Formula

| S. No | Ingredients | mg/tab |
|---|---|---|
| 1. | Entacapone | 200.00 |
| 2. | Sodium Hydroxide | 19.00 |
| 3. | Microcrystalline Cellulose (Avicel PH 200) | 434.40 |
| 4. | Sodium Stearyl Fumarate | 6.60 |
| 5. | Hydroxy propyl methylcellulose (6 CPS) | 13.10 |
| 6. | Polyethylene Glycol 6000 | 2.46 |
| 7. | Titanium Dioxide | 0.82 |
| 8. | Red Iron Oxide | 0.13 |

Manufacturing Process:

200 mg (29.56% w/w) of Entacapone was sifted through #60 sieve and granulated with solution of 19.0 mg (2.81% w/w) of Sodium hydroxide in 33.33 mg of water. Wet granules were dried at 60° C. and sized through #60 sieve. Dried granules were blended with 434.4 mg (64.21% w/w) of Microcrystalline cellulose (Avicel PH 200) and 6.6 mg (0.98% w/w) of Sodium stearyl fumarate. The lubricated blend was compressed into 660 mg tablets. Thus tablets obtained were coated with coating suspension containing 13.10 mg (1.94% w/w) of Hydroxy propyl methylcellulose 6 cps), 2.46 mg (0.36% w/w) of Polyethylene Glycol 6000, 0.82 mg (0.12% w/w) of Titanium Dioxide and 0.13 mg (0.02% w/w) of Red Iron Oxide.

Example-2

Formula

| S. No | Ingredients | mg/tab | % w/w |
|---|---|---|---|
| 1. | Entacapone | 200.00 | 29.56 |
| 2. | Sodium Hydroxide | 19.00 | 2.81 |
| 3. | Mannitol (Perlitol SD 200) | 302.00 | 44.64 |
| 4. | Microcrystalline cellulose (Avicel PH 200) | 129.10 | 19.08 |
| 5. | Sodium Stearyl Fumarate | 9.90 | 1.46 |
| 6. | Hydroxy propyl methylcellulose (6 CPS) | 13.10 | 1.94 |
| 7. | Polyethylene Glycol 6000 | 2.46 | 0.36 |
| 8. | Titanium Dioxide | 0.82 | 0.12 |
| 9. | Red Iron Oxide | 0.13 | 0.02 |

Manufacturing Process:

200 mg (29.56% w/w) of Entacapone was sifted through #60 sieve and granulated with solution of 19.0 mg (2.81% w/w) of Sodium hydroxide in 33.33 mg of water. Wet granules were dried at 60° C. and sized through #60 sieve. Dried granules were blended with 129.1 mg (19.08% w/w) of Microcrystalline cellulose (Avicel PH 200), 302.0 mg (44.64% w/w) of Mannitol (Pearlitol SD 200) and 6.6 mg (0.98% w/w) of Sodium stearyl fumarate. The lubricated blend was compressed into 660 mg tablets. Thus tablets obtained were coated with coating suspension containing 13.10 mg (1.94% w/w) of Hydroxy propyl methylcellulose (6 CPS), 2.46 mg (0.36% w/w) of Polyethylene glycol 6000, 0.82 mg (0.12% w/w) of Titanium Dioxide and 0.13 mg (0.02% w/w) of Red Iron oxide Example-3

Formula

| S. No | Ingredients | mg/tab |
|---|---|---|
| 1. | Entacapone | 200.00 |
| 2. | Disodium Hydrogen Phosphate | 33.72 |
| 3. | Microcrystalline Cellulose (Avicel PH 200) | 416.38 |
| 4. | Sodium Stearyl Fumarate | 9.90 |
| 5. | Hydroxy propyl Methylcellulose (6 CPS) | 13.10 |
| 6. | Polyethylene Glycol 6000 | 2.46 |
| 7. | Titanium Dioxide | 0.82 |
| 8. | Red Iron Oxide | 0.13 |

Manufacturing Process:

200 mg (29.56% w/w) of Entacapone was sifted through #60 sieve and granulated with solution of 33.72 mg (4.98% w/w) of Disodium hydrogen phosphate in 100 mg of water. Wet granules were dried at 60° C. and sized through #60 sieve. Dried granules were blended with 416.38 mg (61.55% w/w) of Microcrystalline cellulose (Avicel PH 200) and 9.9 mg (1.46% w/w) of Sodium stearyl fumarate. The lubricated blend was compressed into 660 mg tablets. Thus tablets obtained were coated with coating suspension containing 13.10 mg (1.94% w/w) of Hydroxy propyl methylcellulose 6 cps, 2.46 mg (0.36% w/w) of Polyethylene glycol 6000, 0.82 mg (0.12% w/w) of Titanium dioxide and 0.13 mg (0.02% w/w) of Red Iron Oxide.

Example-4

Formula

| S. No | Ingredients | mg/Cap |
| --- | --- | --- |
| 1. | Entacapone | 200.00 |
| 2. | Sodium Hydroxide | 13.50 |
| 3. | Mannitol (Perlitol SD 200) | 80.50 |
| 4. | Hydrogenated Castor Oil | 6.00 |
| 5. | Hard Gelatin Capsule (Size 0) | 96.00 |

Manufacturing Process:

200 mg (50.51% w/w) of Entacapone was sifted through #60 sieve and granulated with solution of 13.5 mg (3.41% w/w) of Sodium hydroxide in 33.33 mg of water. Wet granules were dried at 60° C. and sized through #60 sieve. Dried granules were blended with 80.5 mg (20.31% w/w) of Mannitol (Perlitol SD 200) and 6.0 mg (1.52% w/w) of Hydrogenated castor oil. 300 mg of lubricated blend was filled into Hard gelatin capsule (Size 0).

Those skilled in the art will recognize that while specific embodiments have been illustrated and described, various modifications and changes may be made without departing from the spirit and scope of the invention.

Other embodiments of the invention will be apparent to those skilled in the from the consideration of the specification and practice of the invention disclosed herein. It is also intended that the specification and examples be considered as exemplary only, with true scope and spirit of the invention being indicated by the following claims.

The references discussed herein are specifically incorporated by reference in their entirety.

Example: 5

Formula

| S. NO | Ingredients | mg/Tab |
| --- | --- | --- |
| 1 | Entacapone | 200 |
| 2 | Sodium Hydroxide | 19 |
| 3 | Levodopa | 150 |
| 4 | Carbidopa | 37.5 |
| 5 | Mannitol | 105.89 |
| 6 | Polyvinylpyrrolidone(K30) | 6.61 |
| 7 | Magnesium Stearate | 10 |
| 8 | Hydroxypropyl Methylcellulose(6 cps) | 13.1 |
| 9 | Polyethylene Glycol 6000 | 2.46 |
| 10 | Titanium Dioxide | 0.82 |
| 11 | Red Iron Oxide | 0.13 |

Manufacturing Process:

200 mg (36.7% w/w) of Entacapone is sifted through #60 sieve and granulated with 19 mg (3.5% w/w) of Sodium Hydroxide in 33.33 mg of water. Wet granules are dried at 60° C. and sized through #60 sieve. 150 mg (27.5% w/w) of Levodopa, 37.5 mg (6.9% w/w) of Carbidopa, 105.89 mg (19.4% w/w) of Mannitol are sifted through #40 and blended. 6.61 mg (1.2% w/w) of Polyvinylpyrrolidone is dissolved in water and granulated levodopa carbidopa blend. Wet granules are dried at 60° C. and sized through #0.8 mm sieve. Entacapone granules and levodopa carbidopa granules are blended with 10 mg (1.8% w/w) stearate and blend compressed into tablets of 529 mg average weight. Thus tablets obtained are coated with coating suspension containing 13.1 (2.4% w/w) of Hydroxypropyl Methylcellulose 6 cps, 2.46 mg (0.5% w/w) of Polyethylene Glycol 6000, 0.82 mg (0.2% w/w) of Titanium Dioxide, 0.13 mg (0.02% w/w) of Red Oxide iron.

Example: 6

Formula

| S. NO | Ingredient | mg/Capsules |
| --- | --- | --- |
| 1 | Entacapone | 200 |
| 2 | Sodium Hydroxide | 19 |
| 3 | Levodopa | 150 |
| 4 | Carbidopa | 37.5 |
| 5 | Mannitol | 104.5 |
| 6 | Polyvinylpyrrolidone(K30) | 5 |
| 7 | Magnesium Stearate | 6 |
| 8 | Hard Gelatin Capsule Size 'O' | 96 |

Manufacturing Process:

200 mg (32.4% w/w) of Entacapone is sifted through #60 sieve and granulated with 19 mg (3.1% w/w) of Sodium Hydroxide in 33.33 mg of water. Wet granules are dried at 60° C. and sized through #60 sieve. 150 mg (24.3% w/w) of Levodopa, 37.5 mg (6.1% w/w) of Carbidopa, 104.5 mg (16.9% w/w) of Mannitol are sifted through #40 and blended. 5 mg (0.8% w/w) of Polyvinylpyrrolidone is dissolved in water and granulated levodopa carbidopa blend. Wet granules are dried at 60° C. and sized through #0.8 mm sieve. Entacapone granules and levodopa carbidopa granules are blended with 6 mg (1% w/w) magnesium stearate and blend filled into Size 'O' capsules of average fill weight 522 mg.

Example: 7

Formula

| S. No | Ingredients | mg/Cap |
| --- | --- | --- |
| 1. | Nitecapone | 200.00 |
| 2. | Sodium Hydroxide | 13.50 |
| 3. | Mannitol (Perlitol SD 200) | 80.50 |
| 4. | Hydrogenated Castor Oil | 6.00 |
| 5. | Hard Gelatin Capsule (Size 0) | 96.00 |

Manufacturing Process:

200 mg (50.51% w/w) of Nitecapone is sifted through #60 sieve and granulated with solution of 13.5 mg (3.41% w/w) of Sodium hydroxide in 33.33 mg of water. Wet granules are dried at 60° C. and sized through #60 sieve. Dried granules are blended with 80.5 mg (20.31% w/w) of Mannitol (Perlitol SD 200) and 6.0 mg (1.52% w/w) of Hydrogenated castor oil. 300 mg of lubricated blend is filled into Hard gelatin capsule (Size 0).

Example-8

Dissolution Profile of Entacapone Tablets

Dissolution in pH 5.8 phosphate buffer, basket@100 rpm.

| Product | Batch No. | Dissolution in % | | | |
|---|---|---|---|---|---|
| | | 15 min | 30 min | 45 min | 60 min |
| Comtan (Reference) | F0125 | 98.63 | 99.03 | 99.77 | 100.23 |
| Entacapone Tablets 200 (Test) | Example-1 | 92.13 | 93.82 | 95.37 | 96.97 |

We claim:

1. A pharmaceutical composition comprising entacapone or nitecapone and one or more alkalizing agent optionally with other active ingredient, without incorporating crosslinked cellulose derivative, which is croscarmellose sodium.

2. A pharmaceutical composition according to claim 1, wherein said other active ingredient is carbidopa and/or levodopa.

3. A pharmaceutical composition according to claim 1, wherein said alkalizing agent is selected from the group of sodium hydroxide, potassium hydroxide, sodium dihydrogen phosphate, disodium hydrogen phosphate, sodium carbonate, sodium bicarbonate, potassium hydrogen phosphate, dipotassium hydrogen phosphate, tripotassium phosphate.

* * * * *

UNITED STATES PATENT AND TRADEMARK OFFICE
CERTIFICATE OF CORRECTION

| | | |
|---|---|---|
| PATENT NO. | : 8,772,346 B2 | Page 1 of 1 |
| APPLICATION NO. | : 12/097453 | |
| DATED | : July 8, 2014 | |
| INVENTOR(S) | : Gour et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 684 days.

Signed and Sealed this
Eighteenth Day of August, 2015

Michelle K. Lee
*Director of the United States Patent and Trademark Office*